United States Patent [19]

Germanas et al.

[11] 3,963,643

[45] June 15, 1976

[54] METHOD OF CATALYST MANUFACTURE

[75] Inventors: Dalia Germanas, Des Plaines; Ernest L. Pollitzer, Skokie, both of Ill.

[73] Assignee: Universal Oil Products Company, Des Plaines, Ill.

[22] Filed: June 30, 1975

[21] Appl. No.: 592,134

Related U.S. Application Data

[63] Continuation-in-part of Ser. No. 462,891, April 22, 1974, abandoned, which is a continuation-in-part of Ser. No. 293,237, Sept. 28, 1972, abandoned.

[52] U.S. Cl. .............................. 252/442; 252/441; 260/683.68; 260/683.75
[51] Int. Cl.² ...................... B01J 27/08; B01J 27/10
[58] Field of Search .......................... 242/441, 442

[56] References Cited

UNITED STATES PATENTS

| 3,366,705 | 1/1968 | Giannetti et al. ............... 252/441 X |
| 3,449,264 | 6/1969 | Myers ................................. 252/441 |
| 3,553,281 | 1/1971 | Gohle et al. ..................... 252/441 X |

*Primary Examiner*—Patrick P. Garvin
*Attorney, Agent, or Firm*—James R. Hoatson, Jr.; Robert W. Welch; William H. Page II

[57] ABSTRACT

Alumina containing a platinum group metal is treated in contact with a Friedel Crafts metal halide, and in contact with a polyhalo compound, such as carbon tetrachloride, to produce an improved hydrocarbon conversion catalyst.

11 Claims, No Drawings

METHOD OF CATALYST MANUFACTURE

RELATED APPLICATIONS

This is a continuation-in-part of a copending application Ser. No. 462,891, filed Apr. 22, 1974, now abandoned which is in turn a continuation-in-part of a copending application Ser. No. 293,237, filed Sept. 28, 1972 now abandoned.

It has been shown that alumina containing a platinum group metal, typically platinum, is particularly useful with respect to the isomerization of paraffin hydrocarbons when treated with a Friedel Crafts metal halide, such as aluminum chloride. More recently, certain polyhalo compounds other than Friedel Crafts metal halides, notably carbon tetrachloride, have been employed to treat a platinum-containing alumina catalyst in the manufacture of a catalyst similarly useful for the low temperature isomerization of paraffin hydrocarbons. It has now been discovered that a substantially improved low temperature isomerization catalyst is obtained when the alumina, containing a platinum group metal, is sequentially treated with said Friedel Crafts metal halide and said polyhalo compound, the improvement being particularly noteworthy where the Friedel Crafts metal halide treatment precedes the polyhalo compound treatment. Thus, in one of its broad aspects, the present invention embodies a method of catalyst manufacture, and comprises the steps of compositing from about 0.1 to about 5 wt. % platinum group metal with alumina; reacting the resultant composite with a Friedel Crafts metal halide in an amount sufficient to introduce from about 2 to about 15 wt. % combined halogen into the composite; and thereafter contacting the composite at a temperature of from about 100° to about 600° C. in a non-reducing atmosphere with a polyhalo compound containing at least two chlorine atoms and selected from the group consisting of methylene halide, haloform, methylhaloform, carbon tetrahalide, sulfur dihalide, sulfuryl halide, thionyl halide, and thiocarbonyl tetrahalide, in sufficient amount to add at least 0.1% combined halogen to the composite.

A more preferred embodiment of this invention is in a method of catalyst manufacture consisting essentially of treating alumina containing from about 0.1 to about 2.0 wt. % platinum, in a hydrogen atmosphere in contact with aluminum chloride, and reacting the aluminum chloride with said alumina with the formation of a composite containing from about 2.0 to about 6.0 wt. % combined chloride, and treating said composite in a nitrogen atmosphere at a temperature of from about 150° to about 350° C. in contact with carbon tetrachloride and adding from about 0.1 wt. % to about 5 wt. % combined chloride to said composite.

The alumina employed in the manufacture of the catalyst of this invention may be any of the various hydrous aluminum oxides or alumina gels such as boehmite, gibbsite, bayerite, and the like. Activated aluminas, such as have been thermally treated at a temperature in excess of about 400° C. with the elimination of at least a portion of the chemically and/or physically combined water and hydroxyl groups commonly associated therewith, are particularly suitable. Preferably, the alumina is an activated alumina characterized by a surface area of from about 100 to about 500 $m^2$/gm, especially gamma- and eta-alumina prepared by a thermal treatment at a temperature generally in the range of from about 400° to about 850° C.

The alumina component, which also serves as a carrier material or support for the other catalyst components, is advantageously employed substantially free of sodium, say less than about 0.5 wt. %. The alumina will typically be utilized in a shape or form determinative of the shape or form of the final catalyst product, e.g., spheres, pills, granules, extrudates, powder, etc. The catalyst of this invention is preferably, although not necessarily, utilized in the form of spheroidal particles, and spheroidal alumina particles are conveniently and advantageously prepared sodium-free by the well-known oil drop method as described in U.S. Pat. No. 2,620,314. Briefly, an alumina sol, such as results from digesting aluminum in hydrochloric acid under controlled conditions, is dispersed as droplets in a hot oil bath whereby gelation occurs with the formation of spheroidal gel particles. In this type of operation, the alumina is set chemically utilizing ammonia as a neutralizing or setting agent. Usually, the ammonia is furnished by an ammonia precursor such as hexamethylenetetramine which is included in the sol. Only a fraction of the ammonia precursor is hydrolyzed or decomposed to ammonia in the relatively short period during which the initial gelation occurs. During the subsequent aging process, the residual ammonia precursor retained in the gel particles continues to hydrolyze and effect further polymerization of the alumina whereby desirable pore characteristics are established. After a suitable aging period, usually from about 10 to about 24 hours at a temperature in the 50°–105° C. range, the alumina spheres are washed, dried, and calcined or activated at a temperature of from about 500° to about 850° C.

Although the invention is directed to the manufacture of a catalyst containing a platinum group metal, i.e., platinum, palladium, rhodium, ruthenium, osmium and iridium, platinum is a preferred catalyst component. The platinum group metal is suitably composited with the alumina utilizing impregnating techniques known to the art. For example, the alumina particles are suspended, dipped, soaked or otherwise immersed in an aqueous solution of a soluble platinum group metal compound. Suitable compounds include platinum chloride, chloroplatinic acid, ammonium chloroplatinate, dinitrodiamino platinum, palladium chloride, chloropalladic acid, and the like. It is common practice to impregnate the alumina with an aqueous chloroplatinic acid solution acidified with hydrochloric acid to facilitate an even distribution of platinum on the alumina, and the resulting composite will in this and similar cases invariably contain combined halogen, although the combined halogen will generally be less than about 1.5 wt. % of the composite. In any case, the alumina is preferably maintained in contact with the impregnating solution at ambient temperature conditions for a brief period, preferably for at least about 30 minutes, and the impregnating solution thereafter evaporated substantially to dryness. For example, a volume of alumina particles is immersed in a substantially equal volume of impregnating solution in a steam-jacketed rotary steam dryer and tumbled therein for a brief period at room temperature. Steam is thereafter applied to the dryer jacket to expedite evaporation of the solution and recovery of substantially dry impregnated alumina particles.

The dried composite will generally be calcined at a temperature of from about 375° to about 595° C. in an air atmosphere to convert the platinum group metal component substantially to the oxide form. In a preferred embodiment of this invention, the alumina-platinum group metal composite utilized as a starting material is prepared in a reduced form. Suitably, the composite is treated in a substantially water-free hydrogen atmosphere at a temperature of from about 425° to about 650° C. to insure a uniform and finely divided dispersion of the platinum group metal component on the alumina.

Pursuant to the preferred method of manufacture, the alumina-platinum group metal starting material is treated first in contact with a Friedel Crafts metal halide at conditions to react said metal halide with said alumina with the formation of a composite containing from about 2 to about 15 wt. % combined halogen. The alumina-platinum group metal starting material is suitably treated in contact with a Friedel Crafts metal halide in accordance with prior art practice whereby the Friedel Crafts metal halide is vaporized and sublimed on the alumina-platinum group metal composite. The process is facilitated by contacting the alumina-platinum group metal composite with Friedel Crafts metal halide vapors diluted with hydrogen or other inert diluent gas. Reaction of the Friedel Crafts metal halide with the alumina will occur, at least to some extent, during the sublimation process. However, a subsequent heat treatment of the Friedel Crafts metal halide in contact with the alumina at a temperature somewhat in excess of the vaporization temperature of the Friedel Crafts metal halide is a preferred practice. The subsequent heat treatment, generally at a temperature of from about 300° to about 600° C. depending upon the particular Friedel Crafts metal halide employed, serves to further the reaction of the Friedel Crafts metal halide with the alumina while effecting vaporization and separation of unreacted Friedel Crafts metal halide, the final catalyst composite being substantially free thereof. Various Friedel Crafts metal halides can be employed although not necessarily with an equivalent degree of improvement. The Friedel Crafts metal halide is preferably a Friedel Crafts metal chloride, for example, aluminum chloride, antimony pentachloride, beryllium chloride, ferric chloride, gallium tetrachloride, stannic chloride, titanium tetrachloride, zinc chloride, zirconium chloride, and the like. In a preferred embodiment of this invention, the Friedel Crafts metal halide is aluminum chloride. The aluminum chloride will sublime at about 178° C. and a suitable vaporization temperature is in the range of from about 180° to about 550° C. The amount of aluminum chloride which sublimes onto the alumina-platinum group metal composite reaches a maximum at any given temperature in excess of about 178° C. As heretofore indicated, in addition to vaporizing and subliming onto the alumina-platinum group metal composite, the aluminum chloride also reacts with the alumina with the evolution of hydrogen chloride. Subsequent heat treatment at a temperature somewhat in excess of the sublimation temperature and generally not exceeding about 600° C. serves to further the reaction and to vaporize unreacted aluminum chloride for separation from the composite, for example, in a stream of inert diluent gas such as nitrogen, hydrogen, etc. In any case, the catalyst composite at this stage will contain from about 2 to about 15 wt. % combined halogen, probably although not necessarily in the form of an oxyaluminum chloride, and be substantially free of unreacted Friedel Crafts metal halide.

Pursuant to the method of this invention, the described aluminaplatinum group metal composite containing from about 2 to about 15 wt. % combined halogen is further treated in contact with a polyhalo compound containing at least 2 chlorine atoms and selected from the group consisting of methylene halide, haloform, methylhaloform, carbon tetrahalide, sulfur dihalide, sulfuryl halide, thionyl halide, and thiocarbonyl tetrahalide. Suitable polyhalo compounds thus include methylene chloride, chloroform, methylchloroform, carbon tetrachloride, sulfur dichloride, sulfuryl chloride, thionyl chloride, thiocarbonyl tetrachloride, and the like. In any case, the polyhalo compound must contain at least two chlorine atoms attached to the same carbon or sulfur atom.

While the first described treatment of the alumina-platinum group metal composite with a Friedel Crafts metal halide may, and preferably is, effected in a reducing atmosphere, treatment in contact with the polyhalo compound requires a non-reducing atmosphere to yield an active catalyst. The alumina-platinum group metal composite is suitably treated in contact with the polyhalo compound per se, but preferably diluted in a non-reducing gas such as nitrogen, air, oxygen, and the like. Said composite is suitably treated at a temperature of from about 100° to about 600° C. in contact with the polyhalo compound over a period of from about 0.2 to about 5 hours to add at least 0.1 wt. % combined halogen thereto. The nature of the combined halogen resulting from the Friedel Crafts metal halide treatment is not necessarily that of the combined halogen resulting from the polyhalo compound treatment. That they are not the same is evidenced by the fact that the improvement in catalyst activity is not observed when the combined halogen level is achieved solely by the Friedel Crafts metal halide treatment, nor is it observed when the combined halogen level is achieved solely by the polyhalo compound treatment. Further, the improvement is not as substantial when the order of treatment is reversed, that is, when the aluminaplatinum group metal composite is first treated with a polyhalo compound and thereafter with the Friedel Crafts metal halide. Of the polyhalo compounds, carbon tetrachloride is preferred.

Catalysts manufactured by the method of this invention are useful to effect a variety of hydrocarbon conversion reactions involving reaction conditions comprising temperatures in the 25°–760° C. range. For example, the catalysts are useful in effecting the hydrocracking of heavy oils to form petroleum products boiling in the middle distillate range utilizing a temperature of from about 260° to about 760° C. and pressures of from about 500 to about 1000 psig. The catalyst compositions of this invention are particularly useful to effect isomerization of isomerizable paraffinic hydrocarbons including n-butane, n-pentane, n-hexane, n-heptane, n-octane, or mixtures thereof, and also the isomerization of slightly branched chain saturated hydrocarbons to more highly branched chain saturated hydrocarbons such as the isomerization of 2- or 3-methylpentane to 2,2- and 2,3-dimethylbutane, and also the isomerization of naphthenes, for example, the isomerization of dimethylcyclopentane to methylcyclohexane, methylcyclopentane to cyclohexane, and the like, at isomerization reaction conditions. The catalysts are especially advantageous to effect low temperature isomerization of straight chain hydrocarbons containing 4 to 6 carbon atoms.

Isomerization of isomerizable paraffinic hydrocarbons as herein contemplated is effected at a relatively low temperature in the range of from about 65° to about 235° C. The hydrocarbon feed stock is treated in admixture with hydrogen utilizing a hydrogen-hydrocarbon mole ratio of from about 0.25:1 to about 20:1 at a pressure ranging from atmospheric to about 2000 psig. In a continuous type of operation liquid hourly space velocities of from about 0.5 to about 10 are suitably employed.

The following examples are comparative examples presented in illustration of the improvement derived from the practice of this invention and are not intended as an undue limitation on the generally broad scope of the invention as set out in the appended claims.

EXAMPLE I

Sodium-free gamma-alumina spheres of about 1/16 inch diameter and containing 0.3 wt. % combined chloride were prepared by the described oil-drop method. The spheres were impregnated with 0.4 wt. % platinum from an aqueous chloroplatinic acid solution by immersing the spheres in the solution and evaporating the solution to dryness in contact with the spheres in a rotary steam evaporator. The dried, impregnated spheres were subsequently calcined at 500°–550° C., first in a stream of air for 2 hours and then in a stream of hydrogen for 1 hour. About 50 grams of aluminum chloride was then vaporized and passed in contact with 125 grams of the reduced, platinum-impregnated spheres utilizing hydrogen as a carrier gas at 750–1000 cubic centimeters per minute. The aluminum chloride treatment was effected over a period of about 1.5 hours at 550° C., the spheres being thereafter flushed with hydrogen for about 1 hour at 600° C. Thereafter, 60 grams of carbon tetrachloride was passed in contact with the spheres using nitrogen as a carrier gas at about 2000 cubic centimeters per minute. The carbon tetrachloride treatment was effected over a period of about 1.5 hours at 300° C. The catalyst was then flushed with nitrogen for 1 hour at 300° C. to remove unreacted carbon tetrachloride. The finished catalyst, containing 6.00 wt. % combined chloride, is referred to hereinafter as Catalyst A.

EXAMPLE II

As heretofore stated, the improved activity of the catalyst of this invention is dependent on the order in which the aluminum chloride and carbon tetrachloride treatments occur. Preferably, as in Example I, the aluminum chloride treatment precedes the carbon tetrachloride treatment. In this example, subsequently utilized as a comparative example with the catalyst of Example I, the order of treatment is reversed. Thus, about 60 grams of carbon tetrachloride was passed in contact with 125 grams of the reduced platinum-impregnated alumina spheres using nitrogen as a carrier gas. The carbon tetrachloride treatment was for a period of about 1.5 hours at 300° C. The spheres were flushed with nitrogen at 300° C. after which 50 grams of aluminum chloride was vaporized and passed in contact therewith utilizing hydrogen as a carrier gas. The aluminum chloride treatment was at 550° C. over a 1.5 hour period after which the spheres were flushed with hydrogen at 600° C. for 1 hour. The finished catalyst, containing 5.71 wt. % combined chloride, is referred to hereinafter as Catalyst B.

It is generally recognized that catalysis involves a highly empirical and unpredictable art. Minor variations in the formulation or method of manufacture of a catalyst may result in a dramatic and unexpected improvement in the catalyst product. The improvement may be the result of an undetermined and minor alteration of the physical and/or chemical composition of the catalyst product not readily apparent but for the unexpected activity, selectivity and/or stability of the catalyst product with respect to a given chemical reaction. In the present case, it has been found that the order in which the aluminum chloride and carbon tetrachloride treatments occur has a significant and unexpected effect on catalyst activity with respect to the low temperature isomerization of n-pentane and n-hexane to form octane-improving branched-chain isomers thereof, and this improvement becomes increasingly apparent as the reaction temperature is decreased.

The catalysts of Example I and II were evaluated with respect to the low temperature isomerization of n-pentane and n-hexane to isopentane and 2,2-dimethylbutane respectively. Thus, a 50 cubic centimeter volume of catalyst was disposed as a fixed bed in a tubular reactor and a hydrocarbon feed stock, comprising 50 mol % n-pentane and 50 mol % n-hexane admixed with hydrogen to provide a hydrocarbon/hydrogen mole ratio of about 8, was charged in contact therewith at liquid hourly space velocities of 2 and 4. The pressure was maintained at 100 psig, with temperatures ranging from about 120° to about 140° C. The conversion of each of the n-pentane and n-hexane to the desired octane-improving isomers at temperatures ranging from about 120° to about 140° C., and at the indicated liquid hourly space velocities, is set out in Table I below. It is readily apparent that Catalyst A, prepared according to the method of this invention, is increasingly more active than Catalyst B as the temperature decreased. The reported conversion is in each case conversion to the desired octane improving isomer and does not necessarily represent the total isomerization efficiency of the catalyst.

TABLE I

| REACTION CONDITIONS | | % CONVERSION TO | | | |
|---|---|---|---|---|---|
| | | iso-pentane | | 2,2-dimethyl-butane | |
| Temp., °C. | LHSV | Cat. A | Cat. B | Cat. A | Cat. B |
| 140 | 4 | 68.5 | 51.8 | 28.7 | 19.2 |
| 120 | 2 | 65.4 | 42.5 | 33.8 | 19.0 |

EXAMPLE III

About 50 grams of aluminum chloride was vaporized and passed in contact with 125 grams of the reduced, platinum-impregnated spheres employed in the preparation of the catalysts of Examples I and II utilizing hydrogen as a carrier gas at 750–1000 cubic centimeters per minute. The aluminum chloride treatment was effected over a period of about 1.5 hours at 550° C., the spheres being thereafter flushed with hydrogen for about 1 hour at 600° C. Thereafter, 60 grams of carbon tetrachloride was passed in contact with the spheres using nitrogen as a carrier gas at about 2000 cubic centimeters per minute. The carbon tetrachloride treatment was in this case effected over a period of about 1.5 hours at 280° C. The catalyst was then flushed with nitrogen for 1 hour at 300° C. to remove unreacted carbon tetrachloride. The finished catalyst contained 5.94 wt. % combined chloride. The catalyst of this example, prepared in accordance with the method of this invention, was evaluated in the described manner. The test results are set out in Table II, the catalyst of this example being referred to as Catalyst C.

EXAMPLE IV

As heretofore stated, the improved activity of the catalyst of this invention is dependent on the order in which the aluminum chloride and carbon tetrachloride treatments occur. Preferably, as in Examples I and III, the aluminum chloride treatment precedes the carbon tetrachloride treatment. In this example, presented as a comparative example with the catalyst of Example III, the order of treatment is again reversed, all other parameters being as described in Example III. Thus, about 60 grams of carbon tetrachloride was passed in contact with 125 grams of the reduced platinum-impregnated alumina spheres using nitrogen as a carrier gas. The carbon tetrachloride treatment was, as in Example III, for a period of about 1.5 hours at 280° C. The spheres were flushed with nitrogen at 300° C. after which 50 grams of aluminum chloride was vaporized and passed in contact therewith utilizing hydrogen as a carrier gas. The aluminum chloride treatment was at 550° C. over a 1.5 hour period after which the spheres were flushed with hydrogen at 600° C.for 1 hour. The finished catalyst contained 5.64 wt. % combined chloride. The catalyst of this example, hereinafter referred to as Catalyst D, was evaluated in the described manner, the results being reported in Table II below in comparison with the results obtained from the use of Catalyst C.

TABLE II

| REACTION CONDITIONS | | % CONVERSION TO | | | |
|---|---|---|---|---|---|
| | | iso-pentane | | 2,2-dimethyl-butane | |
| Temp., °C. | LHSV | Cat. C | Cat. D | Cat. C | Cat. D |
| 140 | 4 | 67.2 | 25.4 | 28.0 | 5.6 |
| 120 | 2 | 63.9 | 17.6 | 32.4 | 5.2 |

EXAMPLE V

A 50 cubic centimeter volume of the catalyst of Example I was disposed as a fixed bed in a tubular reactor, and a hydrocarbon feed stock comprising n-butane admixed with hydrogen to provide a hydrocarbon/hydrogen mole ratio of about 0.5 was charged in contact therewith at a liquid hourly space velocity of 6.0. Reaction conditions further included a temperature of 180° C. and a pressure of 500 psig. A 49.5% conversion of n-butane was obtained in the once-through operation at the described reaction conditions, and the isomerization efficiency was 99+%.

We claim as our invention:

1. In a method of catalyst manufacture, the steps of compositing from about 0.1 to about 5 wt. % platinum group metal with alumina, reacting the resultant composite with a Friedel Crafts metal halide in an amount sufficient to introduce from about 2 to about 15 wt. % combined halogen into the composite, and thereafter contacting the composite at a temperature of from about 100° to about 600° C. in a non-reducing atmosphere with a polyhalo compound containing at least 2 chlorine atoms selected from the group consisting of methylene halide, haloform, methylhaloform, carbon tetrahalide, sulfur dihalide, sulfuryl halide, thionyl halide, and thiocarbonyl tetrahalide in sufficient amount to add at least 0.1 wt. % combined halogen to the composite.

2. The method of claim 1 further characterized in that said metal halide is in vapor form and is sublimed onto the composite which is then heated to a temperature of from about 300° to about 600° C.

3. The method of claim 1 further characterized in that said platinum group metal is platinum.

4. The method of claim 1 further characterized in that said alumina is gamma-alumina.

5. The method of claim 1 further characterized in that said alumina is eta-alumina.

6. The method of claim 1 further characterized in that said alumina is substantially sodium-free.

7. The method of claim 1 further characterized in that said alumina is gamma-alumina containing from about 0.2 to about 2.0 wt. % platinum.

8. The method of claim 1 further characterized in that said Friedel Crafts metal halide is aluminum chloride.

9. The method of claim 1 further characterized in that said polyhalo compound is carbon tetrachloride.

10. A method of catalyst manufacture consisting essentially of treating alumina containing from about 0.1 to about 2.0 wt. % platinum in a hydrogen atmosphere in contact with aluminum chloride and reacting the aluminum chloride with said alumina with the formation of a composite containing from about 2.0 to about 6.0 wt. % combined chloride, and treating said composite in a nitrogen atmosphere at a temperature of from about 150° C. to about 350° C. in contact with carbon tetrachloride and adding from about 0.1 to about 5 wt. % combined chloride to said composite.

11. A catalyst prepared by the method of claim 1 and consisting essentially of a platinum group metal, alumina and combined halogen.

* * * * *